United States Patent [19]

Takashi et al.

[11] Patent Number: 5,155,235
[45] Date of Patent: Oct. 13, 1992

[54] CATALYST FOR PRODUCING MALEIC ANHYDRIDE FROM BUTANE AND PROCESS FOR PREPARING SAME

[75] Inventors: Jimbo Takashi; Tadamitsu Kiyoura; Yasuo Kogure; Kazuo Kanaya, all of Kanagawa, Japan

[73] Assignee: Mitsui Toatsu Chemicals, Inc., Tokyo, Japan

[21] Appl. No.: 726,185

[22] Filed: Jul. 5, 1991

[30] Foreign Application Priority Data

Jul. 12, 1990 [JP] Japan .................. 2-182702
Oct. 26, 1990 [JP] Japan .................. 2-287223

[51] Int. Cl.$^5$ .................. B01J 27/148; B01J 27/18; C07D 307/34
[52] U.S. Cl. .................. 549/262; 549/259; 549/260; 502/162; 502/209
[58] Field of Search .................. 549/259, 260, 262; 502/162, 209

[56] References Cited

U.S. PATENT DOCUMENTS

| | | | |
|---|---|---|---|
| 2,079,171 | 5/1937 | Huffman | 74/30 |
| 3,931,046 | 1/1976 | Weinstein et al. | 252/429 |
| 4,151,116 | 4/1979 | McDermott | 252/435 |
| 4,209,423 | 6/1980 | Hutchings et al. | 252/435 |
| 4,219,484 | 8/1980 | Milberger et al. | 252/437 |
| 4,283,307 | 8/1981 | Barone et al. | 252/432 |
| 4,360,453 | 11/1982 | Lemanski et al. | 252/435 |
| 4,510,258 | 4/1985 | Suciu et al. | 502/209 |
| 4,511,670 | 4/1985 | Suciu et al. | 502/209 |
| 4,647,673 | 3/1987 | Bremer et al. | 549/260 |
| 4,824,819 | 4/1989 | Edwards et al. | 549/259 |
| 4,855,457 | 8/1989 | Ramzi et al. | 549/260 |
| 4,957,894 | 9/1990 | Haddad et al. | 549/260 |
| 5,021,384 | 6/1991 | Hatano et al. | 549/260 |

FOREIGN PATENT DOCUMENTS

| | | |
|---|---|---|
| 056901 | 8/1982 | European Pat. Off. |
| 084706 | 8/1983 | European Pat. Off. |
| 098039 | 1/1984 | European Pat. Off. |
| 107274 | 5/1984 | European Pat. Off. |
| 53-146992 | 12/1978 | Japan . |
| 54-13483 | 1/1979 | Japan . |
| 54-30114 | 3/1979 | Japan . |
| 57-24643 | 2/1982 | Japan . |
| 57-71641 | 5/1982 | Japan . |
| 57-122944 | 7/1982 | Japan . |
| 57-130552 | 8/1982 | Japan . |
| 57-132550 | 8/1982 | Japan . |
| 58-84045 | 5/1983 | Japan . |
| 58-114735 | 7/1983 | Japan . |
| 59-12759 | 1/1984 | Japan . |
| 59-55350 | 3/1984 | Japan . |
| 59-87049 | 5/1984 | Japan . |
| 145046 | 8/1984 | Japan .................. 549/259 |
| 60-227835 | 11/1985 | Japan . |
| 60-227836 | 11/1985 | Japan . |
| 61-181540 | 8/1986 | Japan . |

Primary Examiner—Cecilia Tsang
Attorney, Agent, or Firm—Burns, Doane, Swecker & Mathis

[57] ABSTRACT

A catalyst for producing maleic anhydride by oxidation of n-butane comprising V,P and additionally Mg or Zr is prepared by (a) heating a pentavalent vanadium compound in an organic medium to reduce at least a part of the pentavalent vanadium to tetravalent vanadium,
(b) reacting the resulting vanadium compound with phosphoric acid in the presence of at least one of a magnesium compound and a zirconium compound to form a catalyst precursor,
(c) separating the resulting catalyst precursor from the organic medium, and
(d) drying and calcining the catalyst precursor.

13 Claims, No Drawings

CATALYST FOR PRODUCING MALEIC ANHYDRIDE FROM BUTANE AND PROCESS FOR PREPARING SAME

BACKGROUND OF THE INVENTION

1. Field of the Invention

The present invention relates to a catalyst for producing maleic anhydride by oxidizing butane and a process for producing the catalyst.

2. Description of the Related Art

Vanadium and phosphorus-containing compounds are used as catalysts for producing maleic anhydride by oxidizing n-butane with an oxygen-containing gas. The vanadium and phosphorus-containing compounds effective as the catalyst are known to be a crystalline compound of the formula, $(VO)_2P_2O_7$. In order to obtain the effective catalyst component, $(VO)_2P_2O_7$, usually $V_2O_5$ is reduced to $V_2O_4$ according to a conventional method, and the $V_2O_4$ is reacted with phosphoric acid to prepare $(VO)_2H_4P_2O_9$, and then this compound is thermally decomposed. In order to produce the catalyst precursor, $(VO)_2H_4P_2O_9$, usually $V_2O_5$, a reducing agent and phosphoric acid are caused to react in an organic solvent, in particular, an alcohol such as isobutyl alcohol and the like and the end product, $(VO)_2H_4P_2O_9$, is separated as a precipitate, and therefore, it is convenient to isolate and recover the effective catalyst component.

Many attempts have been made to add promoter components to vanadium and phosphorus-containing compounds. For example, examples of addition of promoter components are summarized in Burnett et al., Catalyst Today, 1, 537 (1987), but effects of addition and function and mechanism of promoters are not discussed. Examples of using magnesium compounds and zirconium compounds are not disclosed.

In Japanese Patent Application Laid-Open No. 146,992/78 is disclosed a process in which a catalyst precursor is formed by reacting a vanadium compound with phosphoric acid in the presence of an acid stronger than phosphoric acid. In the specification, rare earth elements and 15 other elements including zirconium are mentioned as examples of promoters. However, nothing is specifically explained with regard to the effects of zirconium.

In Japanese Patent Application Laid-Open No. 13,483/79 is proposed a process in which a catalyst precursor is synthesized by subjecting a pentavalent vanadium compound to reduction with a powdered metal or a colloidal metal and at the same time to hydrothermal synthesis. In the specification, magnesium is mentioned as an example of a metal reducing agent, but this method is not preferred since expensive metals are used as a reducing agent. Further, other than the metal reducing agents, 14 elements including zirconium and alkaline earth and alkaline metals are mentioned as promoters. However, nothing is mentioned about the effect resulting from the addition of zirconium.

In Japanese Patent Application Laid-Open No. 30114/79 is disclosed a process in which 23 promoters including magnesium are incorporated in vanadium-phosphorus system catalysts by impregnation. However, according to the working examples, the catalyst containing vanadium and phosphorus can give maleic anhydride in only 49% yield and therefore, is not sufficiently effective for industrial purpose.

In Japanese Patent Application Laid-Open No. 24,643/82 is disclosed an annular catalyst consisting of vanadium and phosphorus compounds. In the specification, 48 elements including magnesium and zirconium are mentioned as examples of metals to be incorporated. There are however no specific explanations on the effects of addition of the metallic elements.

In Japanese Patent Application Laid-Open No. 114,735/83 is described a process for activating vanadium and phosphorus-containing catalysts with oxygen and a reducing gas. In the specification, alkali metals, alkaline earth metals, rare earths and 13 other elements including zirconium are mentioned as possible promoter components. However, nothing is specifically explained with regard to the effect of magnesium, other alkaline earth metals and zirconium.

In Japanese Patent Application Laid-Open No. 12,759/84 is proposed a method wherein a catalyst precursor is recovered by adding water to an organic slurry containing the precursor resulting in separation into two phases. As examples of promoter components, mention is made of alkali metals, alkaline earth metals, lanthanides, an other 23 elements including zirconium. However, nothing is specifically described with regard to the promoter effects of magnesium, other alkaline earth metals and zirconium.

In Japanese Patent Application Laid-Open No. 55,350/84 is disclosed a method for spray drying a catalyst precursor after it has been pulverized and densified. In the specification, mention is made of promoter components such as alkali metals, alkaline earth metals, rare earths, and 24 other elements including zirconium. However, there are contained no specific descriptions with regard to the promoter effects of magnesium, other alkaline earth metals and zirconium.

In Japanese Patent Application Laid-Open No. 145046/84 is described a process for preparing a catalyst by mixing a first component, a crystalline vanadium and phosphorus-containing compound; a second component, an aqueous vanadyl phosphate; a third component, a compound of at least one element selected from magnesium, calcium, strontium and barium; and a fourth component, silica and drying the mixture. However, according to the present inventors' study, the catalyst prepared in such a procedure is not suitable for industrial production due to the low yield of maleic anhydride.

In Japanese Patent Application Laid-Open Nos. 227,835/85 and 227,836/85 is described a process for preparing catalysts in which a vanadium and phosphorus-containing catalyst precursor is admixed with a paste of hydrated zirconium hydroxide. However, according to studies by the present inventors, catalysts prepared in accordance with the process give no significant improvements in the yields of maleic anhydride.

Zirconium is mentioned as a possible promoter component in Japanese Patent Application Laid-Open Nos. 71,641/82; 122,944/82; 130,552/82; 132,550/82; 84,045/83; 87,049/84 and 181,540/86. In the specifications of these patents, nothing is explained on the effects of zirconium.

SUMMARY OF THE INVENTION

An object of the present invention is to provide a catalyst capable of giving a high yield of maleic anhydride.

Another object of the present invention is to provide a method of producing the catalyst.

According to one aspect of the present invention, there is provided a process for preparing a catalyst for producing maleic anhydride from n-butane containing vanadium and phosphorus and additionally at least one of magnesium and zirconium which comprises:

(a) heating a pentavalent vanadium compound in an organic medium to reduce at least a part of the pentavalent vanadium to tetravalent vanadium, (b) reacting the resulting vanadium compound with phosphoric acid in the presence of at least one of a magnesium compound and a zirconium compound to form a catalyst precursor, (c) separating the resulting catalyst precursor from the organic medium, and (d) drying and calcining the catalyst precursor.

According to another aspect of the present invention, there is provided a catalyst for producing maleic anhydride from n-butane containing vanadium and phosphorus and additionally at least one of magnesium and zirconium produced by (a) heating a pentavalent vanadium compound in an organic medium to reduce at least a part of the pentavalent vanadium to tetravalent vanadium, (b) reacting the resulting vanadium compound with phosphoric acid in the presence of at least one of a magnesium compound and a zirconium compound to form a catalyst precursor, (c) separating the resulting catalyst precursor from the organic medium, and (d) drying and calcining the catalyst precursor.

According to a further aspect of the present invention, there is provided a process for producing maleic anhydride comprising oxidizing n-butane with an oxygen-containing gas in the presence of the above-mentioned catalyst.

DESCRIPTION OF THE PREFERRED EMBODIMENTS

Examples of pentavalent vanadium compounds usable in this invention include vanadium pentoxide ($V_2O_5$), and metavanadates, for example, ammonium metavanadate. In usual cases, vanadium pentoxide is used.

The organic medium used in the present invention has two functions; as a reducing agent for pentavalent vanadium compounds and as a reaction solvent.

Examples of the organic medium include alcohols such as methanol, ethanol, n-propyl alcohol, isopropyl alcohol, n-butyl alcohol, isobutyl alcohol, 2-butyl alcohol, amyl alcohol, benzyl alcohol, ethylene glycol, 1,2-propanediol, 1,3-propanediol, 1,2-butanediol, 1,3-butanediol, 1,4-butanediol, diethylene glycol, triethylene glycol, and the like; aldehydes such as benzaldehyde, acetaldehyde, propionaldehyde, and the like; ketones such as acetone, methyl ethyl ketone, and the like; and ethers such as diethyl ether, dibutyl ether, tetrahydrofuran, and the like. These organic media can be used either individually or in the form of a mixture of two or more. Of these media, primary and secondary alcohols are preferable. It can be particularly preferable to use isobutyl alcohol, or a mixture of isobutyl alcohol and benzyl alcohol.

In the reduction step, a pentavalent vanadium compound is reduced in an appropriate organic medium until at least a part of the compound becomes a tetravalent state. For example, a pentavalent compound is mixed with an organic medium and the reduction is carried out with stirring under reflux, and water formed by the reduction is separated and removed from the organic medium.

In the reaction step, the resulting vanadium compound at least a part of which is reduced to the tetravalent state is reacted with phosphoric acid in the presence of a magnesium compound and/or a zirconium compound to produce a catalyst precursor.

According to the present invention, it is important that a magnesium compound and/or a zirconium compound is present when the reaction of the vanadium compound with phosphoric acid is caused.

In other words, if a magnesium compound and/or a zirconium compound is added to the catalyst system after a catalyst active component, $(VO)_2P_2O_7$ or a catalyst precursor, $(VO)_2H_4P_2O_9$ has been already formed, a catalyst giving a high yield of maleic anhydride can not be obtained.

The time at which, for example, a magnesium compound is added to a vanadium compound may be before or after the reduction step as long as the time is before the reaction of the vanadium compound with phosphoric acid occurs.

In the reaction step, there may be used commercially available 85% phosphoric acid. It is however preferable to use substantially anhydrous phosphoric acid. The wording "substantially anhydrous" means that phosphoric acid which is formally represented by $H_3PO_4$ is contained in an amount not less than 95% by weight, preferably not less than 98% by weight.

In the catalyst, the atomic ratio of magnesium to the total of vanadium and magnesium is usually in the range of from 0.001 to 0.2, preferably from 0.01 to 0.15. If the ratio is too small, there is attained no improvements in the yield of maleic anhydride, whereas if it is too large, the conversion rate of butane is undesirably lowered.

In the catalyst, the atomic ratio of zirconium to the total of vanadium and zirconium is usually in the range of from 0.001 to 0.2, preferably from 0.01 to 0.15. If the ratio is too small, there is attained no improvements in the yield of maleic anhydride, whereas if it is too large, the conversion rate of butane is undesirably lowered.

In the catalyst, the atomic ratio of phosphorus to the total of vanadium and magnesium is in the range of from 0.9 to 1.2, preferably from 1.0 to 1.1. If the amount of phosphorus is too small, the selectivity to maleic anhydride is lowered, whereas if it is too large, the conversion of butane is lowered.

In the catalyst, the atomic ratio of phosphorus to the total of vanadium and zirconium is usually in the range of from 0.8 to 1.5, preferably from 0.9 to 1.5. If the amount of phosphorus is too small, the selectivity to maleic anhydride is lowered, whereas if it is too large, the conversion of butane is lowered.

As examples of magnesium compounds usable in the invention, mention may be made of inorganic magnesium compounds such as magnesium hydroxide, magnesium carbonate, magnesium nitrate, magnesium oxide, and the like; magnesium salts of organic acids such as magnesium acetate, magnesium oxalate, magnesium citrate, and the like; and complexes of magnesium with organic compounds such as ethylenediaminetetraacetic acid (EDTA), acetylacetone, nitrilotriacetic acid (NTA) and the like. Of these magnesium compounds, complexes of organic compounds and magnesium or salts of magnesium of organic acids are preferable.

As examples of zirconium compounds usable in the invention, mention may be made of inorganic zirconium compounds such as zirconium oxide, zirconium hydroxide, zirconium chloride, zirconium oxychloride, zirconium oxynitrate, zirconium sulfate, zirconium oxyphosphate, and the like; zirconium salts of organic acids such as zirconium oxyacetate and the like; and complexes of zirconium with organic compounds such as ethylenediaminetetraacetic acid (EDTA), acetylacetone, and nitrilotriacetic acid (NTA) and the like. Of these zirconium compounds, complexes of organic compounds and zirconium or salts of zirconium of organic acids are preferable.

The catalyst precursor obtained as above is separated from the organic medium in a conventional manner such as filtration, centrifugation, evaporation to dryness, or the like. In usual cases, the filtration method is employed.

The catalyst precursor separated from the organic medium is then dried, calcined and activated by a known method. Examples of gases usable for the calcining and activation include air, nitrogen, a mixture of air and nitrogen, a mixture of n-butane and air, a mixture of n-butane and nitrogen and the like. The calcining and activation can be carried out at a temperature of from 400° to 600° C.

There is no particular restrictions on the shape of the catalyst It can be in the form of tablets, rings, spheres, microspheres (for fluidized bed), extruded tips, or the like. The catalyst can be shaped by a known method, including compression molding, extrusion molding, and spray drying. The shaping may be effected before or after calcination and activation.

Maleic anhydride can be produced in high yield from n-butane in the presence of a catalyst obtained by the present invention according to the following formula (1).

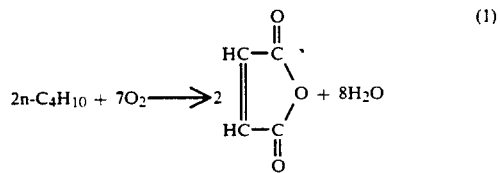

The starting material may be n-butane alone or n-butane containing a small amount of isobutane, butenes, propane, and pentanes.

The reaction of producing maleic anhydride from n-butane may be carried out by using a reactor of a fixed bed type or a fluidized bed type. Upon the reaction, the starting material, n-butane, is usually mixed with air, but there may be used a mixture of air and an inert gas or a mixture of oxygen and an inert gas in place of air.

The concentration of n-butane is 1–5%, preferably 2–4%. In general when the concentration of n-butane is raised while the total gas amount is kept constant, the temperature required for attaining the same n-butane conversion rises.

Further, the higher the concentration of n-butane, the higher the possibility of danger of explosion. However, a higher concentration of n-butane is allowed in a fluidized bed reactor than in a fixed bed reactor. The higher the concentration of n-butane, the higher the concentration of maleic anhydride in the gas flowing out from the outlet of a reactor, and thereby, recovery of maleic anhydride at a later stage becomes easy.

In industrial apparatuses for producing maleic anhydride, the concentration of n-butane in a reaction gas is determined taking the above-mentioned point. The gas mixture may be fed to a reactor at a rate of 0.01–0.5 kg, preferably 0.02–0.1 kg of n-butane per one hour per 1 kg of the catalyst.

The oxidation reaction of n-butane is usually effected at 300°–500° C. The reaction pressure may be reduced pressure, ordinary pressure or high pressure, but the reaction is usually carried out at about ordinary pressure.

The catalyst of the present invention containing vanadium and phosphorus and additionally at least one of magnesium and zirconium gives a higher yield of maleic anhydride from n-butane than conventional catalyst, and it is highly valuable from an industrial point of view.

The present invention is now more particularly described with reference to the following examples which are for the purpose of illustration only and are intended to imply no limitation thereon.

EXAMPLE 1

$V_2O_5$ powder (15.0 g) having a purity of 99% was added with stirring by small portions to 150 ml of a mixture of 60 vol % of isobutyl alcohol and 40 vol % of benzyl alcohol. Then, $V_2O_5$ was reduced by heating the reaction mixture under reflux with stirring for 2 hours at ordinary pressure while water formed by the reaction was removed by means of azeotropy.

After completion of the reflux, the alcohol solution was cooled to room temperature, and 1.9 g of acetylacetonatomagnesium and then 17.9 g of 99% phosphoric acid were added thereto. The atomic ratio of magnesium to the total of vanadium and magnesium was 0.05; and the atomic ratio of phosphorus to the total of vanadium and magnesium was 1.05.

With vigorous stirring, the resulting mixture was heated under reflux for 2 hours while the water formed was removed out of the system by means of azeotropy. The resulting solution was cooled to room temperature and then subjected to filtration to collect the catalyst precursor thus formed, which was washed with isopropyl alcohol and then dried. The dried product was calcined for 3 hours at 500° C. in an atmosphere of nitrogen. The calcined product was pulverized in a mortar, and screened to collect the portion of particles of 350 to 700 μm in size.

Into a fixed-bed flow reactor (made of glass) was charged 1.5 g of the catalyst thus prepared, and an n-butane/air mixture was passed through the reactor at a rate of 50 ml/min. Unreacted butane was analyzed by gas chromatography, and maleic anhydride formed by the reaction was determined by titration.

The reaction temperature was changed in 10° C. increments to effect the activity test, and data were collected at a region around the temperature where the yield of maleic anhydride became the highest. The results are shown in Table 1 and Table 2.

As is clear from Table 1, the lower the concentration of n-butane, the higher the yield of maleic anhydride. In Example 2 et seq., the data at the n-butane concentration of 2% are shown as representative data.

TABLE 1

|  | n-Butane concentration (%) | Reaction temperature (°C.) | n-Butane conversion (%) | Maleic anhydride yield (mol %) |
|---|---|---|---|---|
| Example 1 | 2.0 | 420 | 85.3 | 58.1 |
|  |  | 430 | 93.0 | 60.8 |
|  |  | 440 | 96.0 | 58.1 |

TABLE 1-continued

| n-Butane concentration (%) | Reaction temperature (°C.) | n-Butane conversion (%) | Maleic anhydride yield (mol %) |
|---|---|---|---|
| 1.5 | 410 | 87.1 | 61.5 |
|  | 420 | 91.4 | 64.2 |
|  | 430 | 95.7 | 62.9 |
| 1.0 | 400 | 84.4 | 64.9 |
|  | 410 | 92.0 | 68.1 |
|  | 420 | 96.3 | 67.4 |

EXAMPLE 2

The procedure of Example 1 was repeated except that the atomic ratio of magnesium to the total of vanadium and magnesium was 0.10, and a catalyst was prepared.

The catalyst (1.5 g) was charged into a fixed-bed flow reactor (made of glass) and an n-butane/air mixture was passed through the reactor at a rate of 50 ml/min.

Unreacted butane was analyzed by gas chromatography, and maleic anhydride formed by the reaction was determined by titration. The reaction temperature was changed in 10° C. increments to effect the activity test, and data exhibiting the highest yield of maleic anhydride are shown in Table 2.

EXAMPLE 3

The procedure of Example 1 was repeated except that the atomic ratio of magnesium to the total of vanadium and magnesium was 0.15, and a catalyst was prepared.

Following the procedure of Example 2, the activity test of the resulting catalyst was effected. The result of the reaction is shown in Table 2.

EXAMPLE 4

The procedure of Example 1 was repeated except that magnesium acetate was used in place of acetylacetonatomagnesium, and a catalyst was prepared. The atomic ratio of magnesium to the total of vanadium and magnesium was 0.05 and this is the same as that in Example 1. Following the procedure of Example 2, the activity test of the resulting catalyst was effected. The result of the reaction is shown in Table 2.

EXAMPLE 5-7

The procedure of Example 1 was repeated except that respective 85%, 89% and 94% phosphoric acids were used in place of 99% phosphoric acid, and catalysts were prepared respectively.

The atomic ratio of magnesium to the total of vanadium and magnesium was 0.05 and the atomic ratio of phosphorus to the total of vanadium and magnesium was 1.05, which was the same as that in Example 1.

The activity test was effected by using this catalyst in a manner similar to Example 2. The reaction results are shown in Table 2.

EXAMPLES 8-9

The procedure of Example 1 was repeated except that the atomic ratio of phosphorus to the total of vanadium and magnesium was 1.00 and 1.10, respectively, and catalysts were prepared.

The activity test was effected by using the catalysts. The reaction results are shown in Table 2.

EXAMPLES 10-12

The procedure of Example 1 was repeated except that magnesium hydroxide, magnesium lactate and magnesium citrate, respectively, were used in place of acetylacetonatomagnesium, and respective catalysts were prepared.

The atomic ratio of magnesium to the total of vanadium and magnesium was 0.05, which was the same as that in Example 1.

The activity test was conducted by using these catalysts. The reaction results are shown in Table 2.

COMPARATIVE EXAMPLE 1

The procedure of Example 1 was repeated except that the magnesium compound was not added and 99% phosphoric acid was added in an amount of 17.9 g, and a catalyst was prepared. The activity test was effected. This comparative example was given to show the effect resulted from addition of a magnesium compound.

The reaction results are shown in Table 2 and Table 3.

COMPARATIVE EXAMPLE 2

To 10.0 g of a vanadium, phosphorus-containing catalyst precursor (dried) prepared by the method of Comparative Example 1 and 0.69 g of acetylacetonatomagnesium was added a small amount of water, kneaded in a mortar and dried.

The resulting dry product was calcined in fluidization in a nitrogen atmosphere at 500° C. for 3 hours, and then pulverized in a mortar and screened to collect the portion of particles of 350–700 μm in size.

This comparative example is given for showing that it is not effective to add a magnesium compound after a vanadium, phosphorus-containing catalyst precursor has been formed.

The catalyst was used to effect the activity test in the same way as in Example 2.

The reaction result is shown in Table 2.

COMPARATIVE EXAMPLE 3

The procedure of Comparative Example 2 was repeated except that 0.18 g of magnesium hydroxide was used in place of 0.69 g of acetylacetonatomagnesium, and a catalyst was prepared. The activity test was effected.

The reaction result is shown in Table 2.

COMPARATIVE EXAMPLE 4

To 150 ml of an alcohol mixture of 60 vol % of isobutyl alcohol and 40 vol % of benzyl alcohol was added 15.0 g of $V_2O_5$ powder of a purity of 99% by small portions with stirring, heated under reflux at ordinary pressure, and the reflux was continued with stirring for two hours while removing water formed by means of azeotropy and thereby $V_2O_5$ was reduced.

After completion of the reflux, the resulting alcohol solution was cooled to room temperature and then 17.9 g of 99% phosphoric acid were added thereto. The mixture was stirred for one hour at room temperature and then 1.9 g of acetylacetonatomagnesium was added followed by heating the resulting mixture under reflux for two hours while distilling off water formed from the system by means of azeotropy.

Then a catalyst was prepared following the procedure of Example 1.

This comparative example is given for showing that it is less effective to add a magnesium compound after a vanadium compound and phosphoric acid have been mixed.

The resulting catalyst was used for the activity test in the same way as in Example 2.

The reaction result is shown in Table 2.

TABLE 2

|  | Reaction temperature (°C.) | n-Butane conversion (%) | Maleic anhydride yield (mol %) |
|---|---|---|---|
| Example 1 | 430 | 93.0 | 60.8 |
| Example 2 | 410 | 91.2 | 60.6 |
| Example 3 | 420 | 91.7 | 54.7 |
| Example 4 | 420 | 92.1 | 56.7 |
| Example 5 | 450 | 89.8 | 50.5 |
| Example 6 | 440 | 90.4 | 51.3 |
| Example 7 | 430 | 94.2 | 55.0 |
| Example 8 | 400 | 90.4 | 59.7 |
| Example 9 | 430 | 93.4 | 58.4 |
| Example 10 | 430 | 92.0 | 55.1 |
| Example 11 | 410 | 90.5 | 59.7 |
| Example 12 | 430 | 93.5 | 57.1 |
| Comparative Example 1 | 450 | 86.5 | 47.8 |
| Comparative Example 2 | 390 | 88.3 | 50.0 |
| Comparative Example 3 | 390 | 83.7 | 49.5 |
| Comparative Example 4 | 420 | 91.2 | 50.2 |

TABLE 3

|  | N-Butane concentration (%) | Reaction temperature (°C.) | n-Butane conversion (%) | Maleic anhydride yield (mol %) |
|---|---|---|---|---|
| Comparative Example 1 | 2.0 | 440 | 78.9 | 45.5 |
|  |  | 450 | 86.5 | 47.8 |
|  |  | 460 | 91.9 | 47.5 |
|  | 1.5 | 420 | 87.1 | 50.1 |
|  |  | 430 | 91.4 | 53.4 |
|  |  | 440 | 95.7 | 51.6 |
|  | 1.0 | 410 | 84.4 | 54.2 |
|  |  | 420 | 92.0 | 56.9 |
|  |  | 430 | 96.3 | 55.7 |

EXAMPLE 13

To 150 ml of a mixture of 60 vol % of isobutyl alcohol and 40 vol % of benzyl alcohol were added 15.0 g of $V_2O_5$ powder of 99% in purity by small portions with stirring, heated under reflux at ordinary pressure with stirring for two hours while removing water formed by means of azeotropy, to reduce $V_2O_5$.

After completion of the reflux, the alcohol solution was cooled to room temperature, and then 4.2 g of acetylacetonatozirconium and 17.9 g of 99% phosphoric acid were added thereto.

The atomic ratio of zirconium to the total of vanadium and zirconium was 0.05 and the atomic ratio of phosphorus to the total of vanadium and zirconium was 1.05.

While stirring sufficiently the above-mentioned mixture was heated under reflux for two hours and the resulting water was distilled away from the system by means of azeotropy. The resulting solution was cooled to room temperature and the resulting catalyst precursor was filtered off, and then washed with isopropyl alcohol followed by drying. The product us dried was calcined in a nitrogen atmosphere at 500° C. for 3 hours and pulverized by a mortar and screened to collect the portion of particles of 350-700 μm in size.

The catalyst thus obtained, 1.5 g, was charged into a glass fixed bed flow type reactor and 2% n-butane/air mixed gas was passed through the reactor at a rate of 50 ml/min. Unreacted butane was analyzed by gas chromatography. The resulting maleic anhydride was quantitatively titrated. The reaction result is shown in Table 4.

EXAMPLE 14

The procedure of Example 13 was repeated except that the atomic ratio of zirconium to the total of vanadium and zirconium was 0.10 and the atomic ratio of phosphorus to vanadium and zirconium was 1.05, and a catalyst was prepared. The activity test was carried out. The reaction result is shown in Table 4.

EXAMPLE 15

The procedure of Example 13 was repeated except that the atomic ratio of zirconium to the total of vanadium and zirconium was 0.02 and the atomic ratio of phosphorus to the total of vanadium and zirconium was 1.05, and a catalyst was prepared, and the activity test was effected.

The reaction result is shown in Table 4.

EXAMPLE 16

The procedure of Example 13 was repeated except that zirconium oxyacetate was used in place of acetylacetonatozirconium, and a catalyst was prepared, and the activity test was effected.

The atomic ratio of zirconium to the total of vanadium and zirconium was 0.05. This ratio is the same as that in Example 1.

The reaction result is shown in Table 4.

EXAMPLE 17

The procedure of Example 13 was repeated except that 15.0 g of $V_2O_5$ powder having a purity of 99%, 19.9 g of 85% phosphoric acid and 0.65 g of zirconium oxyacetate were used, and a catalyst was prepared, and the activity test was effected.

The atomic ratio of zirconium to the total of vanadium and zirconium was 0.02 and the atomic ratio of phosphorus to the total of vanadium and zirconium was 1.04. The reaction result is shown in Table 4.

EXAMPLE 18

The procedure of Example 17 was repeated except that the atomic ratio of zirconium to the total of vanadium and zirconium was 0.05 and the atomic ratio of phosphorus to the total of vanadium and zirconium was 1.04, and a catalyst was prepared, and the activity test was effected. The reaction result is shown in Table 4.

EXAMPLE 19

The procedure of Example 13 was repeated except that zirconium oxynitrate was used in place of acetylacetonatozirconium, and the catalyst was prepared, and the activity test was effected. The atomic ratio of zirconium to the total of vanadium and zirconium was 0.05, which was the same as that in Example 13.

The reaction result is shown in Table 4.

EXAMPLE 20

The procedure of Example 13 was repeated except that zirconium oxide was used in place of acetylacetonatozirconium, and a catalyst was prepared, and the activity test was effected.

The atomic ratio of zirconium to the total of vanadium and zirconium was 0.05, which was the same as that in Example 13.

The reaction result is shown in Table 4.

COMPARATIVE EXAMPLE 5

To 10.0 g of a vanadium, phosphorus-containing catalyst precursor (dried) prepared by the method of Comparative Example 1 and 1.5 g of acetylacetonatozirconium was added a small amount of water and kneaded in a mortar and then dried. The dried product was calcined in fluidization in a nitrogen atmosphere at 500° C. for 3 hours and then pulverized in a mortar and screened to collect the portion of particles of 350–700 μm in size.

This comparative example shows that it is not effective to add a zirconium compound after a vanadium, phosphorus-containing catalyst precursor has been formed. The reaction result is shown in Table 4.

COMPARATIVE EXAMPLE 6

To 150 ml of an alcohol mixture of 60 vol % of isobutyl alcohol and 40 vol % of benzyl alcohol was added 15.0 g of $V_2O_5$ powder having a purity of 99% by small portions with stirring, heated under reflux at ordinary pressure, and the reflux was continued with stirring for two hours to reduce $V_2O_5$ while removing water formed by means of azeotropy.

After completion of the reflux, the resulting alcohol solution was cooled to room temperature and then 17.9 g of 99% phosphoric acid was added thereto.

The resulting mixture was stirred at room temperature for one hour, and 4.2 g of acetylacetonatozirconium were added. Then, in a manner similar to Example 13, there were effected dehydration under reflux, filtration, drying, calcination, pulverization and classification.

The atomic ratio of zirconium to the total of vanadium and zirconium was 0.05 and the atomic ratio of phosphorus to the total of vanadium and zirconium was 1.05.

This comparative example shows that it is of little effect to add a zirconium compound after a vanadium compound and phosphoric acid have been mixed.

The reaction result is shown in Table 4.

COMPARATIVE EXAMPLE 7

10.0 g of a vanadium, phosphorus-containing catalyst precursor (dried) prepared by the method of Comparative Example 1 and 1.30 g of zirconium hydroxide sol (23.2 wt % in terms of zirconium oxide) were kneaded in a mortar and dried. The resulting dry product was calcined in fluidization in a nitrogen atmosphere at 500° C. for 3 hours, and pulverized in a mortar and, screened to collect the portion of particles of 350–700 μm in size.

The reaction result is shown in Table 4.

TABLE 4

| | Reaction temperature (°C.) | n-Butane conversion (%) | Maleic anhydride yield (mol %) |
|---|---|---|---|
| Example 13 | 420 | 94.0 | 59.2 |
| Example 14 | 430 | 93.3 | 55.1 |
| Example 15 | 450 | 89.9 | 51.2 |
| Example 16 | 420 | 91.6 | 57.4 |
| Example 17 | 440 | 93.2 | 53.8 |
| Example 18 | 450 | 90.5 | 54.1 |
| Example 19 | 430 | 92.1 | 52.0 |
| Example 20 | 450 | 94.5 | 51.1 |
| Comparative Example 5 | 430 | 88.7 | 45.0 |
| Comparative Example 6 | 440 | 90.0 | 49.2 |
| Comparative Example 7 | 410 | 84.6 | 39.6 |

What is claimed is:

1. A process for preparing a catalyst for producing maleic anhydride from n-butane containing vanadium and phosphorus and additionally at least one of magnesium and zirconium which comprises:

(a) forming a mixture of a vanadium compound in an organic medium with at least one member selected form a magnesium compound and a zirconium compound, wherein the vanadium compound in the organic medium is heated before forming the mixture or as said mixture to reduce at least a part of the pentavalent vanadium in a pentavalent vanadium compound to tetravalent vanadium, (b) reacting the mixture of the organic medium, the vanadium compound at least a part of which is a tetravalent vanadium compound and at least one of said magnesium compound and said zirconium compound with phosphoric acid, (c) separating the resulting catalyst precursor from said organic medium, and (d) drying and calcining the catalyst precursor.

2. The process according to claim 1 in which the organic medium is an alcohol.

3. The process according to claim 1 in which the organic medium is isobutyl alcohol.

4. The process according to claim 1 in which the organic medium is a mixture of isobutyl alcohol and benzyl alcohol.

5. The process according to claim 1 in which the pentavalent vanadium compound is vanadium pentaoxide.

6. The process according to claim 1 wherein the magnesium compound is at least one of the group consisting of a complex of magnesium with an organic compound selected from the group consisting of ethylenediaminetetraacetic acid, acetylacetone and nitrilotriacetic acid, and a magnesium salt of a carboxylic acid.

7. A process for producing maleic anhydride which comprises oxidizing n-butane with an oxygen containing gas in the presence of a catalyst as set forth in claim 1.

8. The process according to claim 5 wherein the magnesium compound is at least one of the group consisting of a complex of magnesium with an organic compound selected form the group consisting of ethylenediaminetetraacetic acid, acetylacetone and nitrilotriacetic acid, and a magnesium salt of a carboxylic acid.

9. The process according to claim 1 wherein the zirconium compound is at least one of the group consisting of a complex of zirconium with an organic compound selected from the group consisting of ethylenediaminetetraacetic acid, acetylacetone and nitrilotriacetic acid, and a zirconium salt of a carboxylic acid.

10. The process according to claim 5 wherein the zirconium compound is at least one of the group consisting of a complex of zirconium with an organic compound selected form the group consisting of ethylenediaminetetraacetic acid, acetylacetone and nitrilotriacetic acid, and a zirconium salt of a carboxylic acid.

11. The process according to claim 1 wherein the atomic ratio of phosphorus to the total of vanadium and magnesium is from 0.9 to 1.2 and the atomic ratios of magnesium to the total of vanadium and magnesium and zirconium to the total of vanadium and zirconium are 0.001 to 0.2.

12. A catalyst for producing maleic anhydride from n-butane containing vanadium and phosphorus and additionally at lest one of magnesium and zirconium produced by
   (a) forming a mixture of a vanadium compound in an organic medium with phosphoric acid in the presence of at least one of a magnesium compound and a zirconium compound to form a catalyst precursor wherein the vanadium compound in the organic medium is heated before forming the mixture or as said mixture to reduce at least a part of the pentavalent vanadium in a pentavalent vanadium compound to tetravalent vanadium,
   (b) reacting the resulting mixture of the organic medium, the vanadium compound at least a part of which is a tetravalent vanadium compound and at leas tone of said magnesium compound and said zirconium compound with phosphoric acid,
   (c) separating the resulting catalyst precursor from said organic medium, and
   (d) drying and calcining the catalyst precursor.

13. The catalyst according to claim 12 wherein the atomic ratio of phosphorus to the total of vanadium and magnesium is from 0.9 to 1.2 and the atomic ratios of magnesium to the total of vanadium and magnesium and zirconium to the total of vanadium and zirconium are 0.001 to 0.2.

* * * * *

UNITED STATES PATENT AND TRADEMARK OFFICE
CERTIFICATE OF CORRECTION

PATENT NO. : 5,155,235
DATED : October 13, 1992
INVENTOR(S) : Jimbo et al.

It is certified that error appears in the above-identified patent and that said Letters Patent is hereby corrected as shown below:

On title page, item [19] change "Takashi et al." to --Jimbo et al.--

On the title page, Section [75] Inventors, Change "Jimbo Takaski" to --Takashi Jimbo--.

In column 13, line 6, delete "form" and insert therefor --from--.

In column 14, line 10, delete "leas tone" and insert therefor --least one--.

Signed and Sealed this

Sixteenth Day of November, 1993

*Attest:*

BRUCE LEHMAN

*Attesting Officer*       *Commissioner of Patents and Trademarks*